(12) United States Patent
Ostrander et al.

(10) Patent No.: US 9,750,899 B2
(45) Date of Patent: Sep. 5, 2017

(54) MEDICAMENT INFORMATION SYSTEM AND METHOD

(71) Applicant: Mylan Inc., Morgantown, WV (US)

(72) Inventors: Kevin Ostrander, Ringoes, NJ (US); John W. Denny, Cary, NJ (US)

( * ) Notice: Subject to any disclaimer, the term of this patent is extended or adjusted under 35 U.S.C. 154(b) by 0 days.

(21) Appl. No.: 14/715,499

(22) Filed: May 18, 2015

(65) Prior Publication Data

US 2015/0250956 A1 Sep. 10, 2015

Related U.S. Application Data

(63) Continuation of application No. 13/907,028, filed on May 31, 2013.
(Continued)

(51) Int. Cl.
*G08B 21/00* (2006.01)
*A61M 5/50* (2006.01)
(Continued)

(52) U.S. Cl.
CPC ....... *A61M 5/5086* (2013.01); *A61B 50/3001* (2016.02); *A61J 7/0076* (2013.01);
(Continued)

(58) Field of Classification Search
CPC ...... H04W 64/00; H04W 48/04; G08B 21/16; B67D 7/3236; A61M 5/172;
(Continued)

(56) References Cited

U.S. PATENT DOCUMENTS

| 4,031,893 A | 6/1977 | Kaplan et al. |
| 4,394,863 A | 7/1983 | Bartner |
| | (Continued) | |

FOREIGN PATENT DOCUMENTS

| CN | 101770683 A | 7/2010 |
| CN | 101796533 A | 8/2010 |
| | (Continued) | |

OTHER PUBLICATIONS

International Search Report and Written Opinion dated Jun. 26, 2015 in PCT/US15/21658.
(Continued)

*Primary Examiner* — George Bugg
*Assistant Examiner* — Anthony D Afrifa-Kyei

(57) ABSTRACT

Various exemplary embodiments relate to a method of using an emergency medicament device. The method includes reading an ID tag from the medicament device using a mobile device; automatically requesting instructions for using the medicament device based on the ID tag; and displaying a video to a user of the mobile device, the video providing instructions for using the medicament device in accordance with approved labeling of the medicament device. Various exemplary embodiments relate to an electronic medicament device including: a reservoir configured to store an amount of medication for treating anaphylaxis; an administration component for administering the medication to a patient; a processor communicatively connected to a memory storing medicament device information; and an identification tag configured to be read by another device, the identification tag providing the medicament device information including identification of instructions for using the medicament device.

20 Claims, 4 Drawing Sheets

Related U.S. Application Data

(60) Provisional application No. 61/732,753, filed on Dec. 3, 2012.

(51) Int. Cl.
| | | |
|---|---|---|
| *A61M 5/20* | (2006.01) | |
| *B65D 83/02* | (2006.01) | |
| *A61J 7/00* | (2006.01) | |
| *G08B 1/08* | (2006.01) | |
| *H04M 3/51* | (2006.01) | |
| *A61M 5/00* | (2006.01) | |
| *G06F 19/00* | (2011.01) | |
| *G08B 3/10* | (2006.01) | |
| *G08B 5/36* | (2006.01) | |
| *G08B 21/18* | (2006.01) | |
| *A61B 50/30* | (2016.01) | |

(52) U.S. Cl.
CPC ............ *A61M 5/002* (2013.01); *A61M 5/20* (2013.01); *B65D 83/02* (2013.01); *G06F 19/323* (2013.01); *G06F 19/3456* (2013.01); *G06F 19/3462* (2013.01); *G06F 19/3468* (2013.01); *G08B 1/08* (2013.01); *G08B 3/10* (2013.01); *G08B 5/36* (2013.01); *G08B 21/182* (2013.01); *H04M 3/5116* (2013.01); *A61M 2205/18* (2013.01); *A61M 2205/3306* (2013.01); *A61M 2205/3368* (2013.01); *A61M 2205/3553* (2013.01); *A61M 2205/3569* (2013.01); *A61M 2205/3584* (2013.01); *A61M 2205/3592* (2013.01); *A61M 2205/52* (2013.01); *A61M 2205/581* (2013.01); *A61M 2205/6054* (2013.01); *A61M 2205/6072* (2013.01)

(58) Field of Classification Search
CPC .. A61M 2205/3553; A61M 2205/3561; A61M 2205/3569; A61M 2205/3592; A61M 2205/502; G06F 19/3468
USPC .................... 340/539.13, 539.12, 686.6
See application file for complete search history.

(56) References Cited

U.S. PATENT DOCUMENTS

| | | |
|---|---|---|
| 4,484,910 A | 11/1984 | Sarnoff et al. |
| 4,640,686 A | 2/1987 | Dalling et al. |
| 4,663,621 A | 5/1987 | Field et al. |
| 4,678,461 A | 7/1987 | Mesa |
| 4,695,954 A | 9/1987 | Rose |
| 4,731,765 A | 3/1988 | Cole et al. |
| 4,795,433 A | 1/1989 | Sarnoff |
| 4,832,682 A | 5/1989 | Sarnoff |
| 4,959,358 A | 9/1990 | Carey |
| 5,085,641 A | 2/1992 | Sarnoff et al. |
| 5,092,843 A | 3/1992 | Monroe et al. |
| 5,102,393 A | 4/1992 | Sarnoff et al. |
| 5,221,024 A | 6/1993 | Campbell |
| 5,354,286 A | 10/1994 | Mesa et al. |
| 5,564,803 A | 10/1996 | McDonald |
| 5,710,551 A | 1/1998 | Ridgeway |
| 5,815,586 A | 9/1998 | Dobbins |
| 5,835,455 A | 11/1998 | Hanson et al. |
| 5,914,675 A | 6/1999 | Tognazzini |
| 5,955,947 A | 9/1999 | Sutsos et al. |
| 5,967,975 A | 10/1999 | Ridgeway |
| 6,032,155 A | 2/2000 | de la Huerga |
| 6,109,774 A | 8/2000 | Holmes et al. |
| 6,158,613 A | 12/2000 | Novosel et al. |
| 6,216,925 B1 | 4/2001 | Garon |
| 6,259,356 B1 | 7/2001 | Tamaoki |
| 6,297,737 B1 | 10/2001 | Irvin |
| 6,401,991 B1 | 6/2002 | Eannone |
| 6,471,087 B1 | 10/2002 | Shusterman |
| 6,529,446 B1 | 3/2003 | de la Huerga |
| 6,595,362 B2 | 7/2003 | Penney et al. |
| 6,633,796 B1 | 10/2003 | Pool et al. |
| 6,707,763 B2 | 3/2004 | Osberg et al. |
| 6,825,753 B2 | 11/2004 | Cardinale et al. |
| 6,880,722 B2 | 4/2005 | Anderson et al. |
| 6,937,150 B2 | 8/2005 | Medema et al. |
| 6,941,274 B1 | 9/2005 | Ramachandran et al. |
| 6,958,691 B1 | 10/2005 | McLennan |
| 7,032,752 B2 | 4/2006 | Krackow |
| 7,138,902 B2 | 11/2006 | Menard |
| 7,191,777 B2 | 3/2007 | Brand |
| 7,449,012 B2 | 11/2008 | Young et al. |
| 7,715,277 B2 | 5/2010 | de la Huerga |
| 7,731,686 B2 | 6/2010 | Edwards |
| 7,749,194 B2 | 7/2010 | Edwards et al. |
| 7,819,116 B2 | 10/2010 | Brand |
| 7,941,534 B2 | 5/2011 | de la Huerga |
| 7,996,106 B2 | 8/2011 | Ervin |
| 8,021,344 B2 | 9/2011 | Edwards |
| 8,044,778 B2 | 10/2011 | Monroe |
| 8,048,035 B2 | 11/2011 | Mesa et al. |
| 8,149,111 B2 | 4/2012 | Monroe |
| 8,172,082 B2 | 5/2012 | Edwards et al. |
| 8,206,360 B2 | 6/2012 | Edwards |
| 8,226,610 B2 | 7/2012 | Edwards |
| 8,249,889 B2 | 8/2012 | Lyons |
| 8,272,562 B2 | 9/2012 | Ziegler |
| 8,361,026 B2 | 1/2013 | Edwards |
| 8,487,738 B2 | 7/2013 | Faries et al. |
| 8,505,959 B2 * | 8/2013 | Darling, III ............ A61G 1/013 280/640 |
| 8,544,645 B2 | 10/2013 | Edwards et al. |
| 8,593,278 B2 | 11/2013 | Churbock et al. |
| 8,670,865 B2 | 3/2014 | Coe |
| 8,744,620 B2 | 6/2014 | Shavelsky et al. |
| 8,753,308 B2 | 6/2014 | Palmer et al. |
| 8,786,729 B2 * | 7/2014 | Peng .................. H04N 9/735 348/222.1 |
| 8,922,367 B2 | 12/2014 | Denny et al. |
| 9,053,520 B2 | 6/2015 | Vik |
| 2001/0028308 A1 | 10/2001 | de La Huerga |
| 2002/0093429 A1 | 7/2002 | Matsushita et al. |
| 2002/0100472 A1 | 8/2002 | Casper et al. |
| 2002/0173875 A1 | 11/2002 | Wallace |
| 2002/0179622 A1 | 12/2002 | Mase |
| 2002/0188259 A1 | 12/2002 | Hickle |
| 2003/0023146 A1 | 1/2003 | Shusterman |
| 2003/0023345 A1 | 1/2003 | Depeursinge |
| 2003/0090364 A1 | 5/2003 | Cardinale et al. |
| 2003/0174554 A1 | 9/2003 | Dunstone |
| 2004/0099676 A1 | 5/2004 | Anderson et al. |
| 2004/0108795 A1 | 6/2004 | Meek |
| 2004/0158350 A1 | 8/2004 | Ostergaard et al. |
| 2004/0173561 A1 | 9/2004 | Wolfe |
| 2004/0210488 A1 | 10/2004 | Doherty |
| 2005/0005934 A1 | 1/2005 | Harvey |
| 2005/0023286 A1 | 2/2005 | Pinney |
| 2005/0113969 A1 | 5/2005 | Spano |
| 2005/0146419 A1 | 7/2005 | Porter |
| 2005/0192705 A1 | 9/2005 | Pinney |
| 2005/0258066 A1 | 11/2005 | Conley |
| 2006/0030891 A1 | 2/2006 | Saltzstein et al. |
| 2006/0089545 A1 | 4/2006 | Ratjen et al. |
| 2006/0125356 A1 | 6/2006 | Meek |
| 2006/0139148 A1 | 6/2006 | Faro |
| 2006/0139149 A1 | 6/2006 | Faro |
| 2006/0242295 A1 | 10/2006 | Husemann et al. |
| 2006/0253096 A1 | 11/2006 | Blakley |
| 2006/0267779 A1 * | 11/2006 | Ishikawa ............... A41D 13/018 340/573.1 |
| 2007/0125100 A1 | 6/2007 | Shoenfeld et al. |
| 2007/0129708 A1 | 6/2007 | Edwards et al. |
| 2007/0156707 A1 | 7/2007 | Fuchs et al. |
| 2007/0185615 A1 | 8/2007 | Bossi |
| 2007/0186923 A1 | 8/2007 | Poutiatine et al. |
| 2007/0197968 A1 | 8/2007 | Pongpairochana et al. |

(56) References Cited

U.S. PATENT DOCUMENTS

| | | |
|---|---|---|
| 2007/0204497 A1 | 9/2007 | de la Huerga |
| 2007/0215018 A1 | 9/2007 | Faries |
| 2007/0227204 A1 | 10/2007 | Shoenfeld |
| 2007/0233001 A1 | 10/2007 | Burroughs et al. |
| 2007/0244598 A1 | 10/2007 | Shoenfeld |
| 2007/0272746 A1 | 11/2007 | Ortiz |
| 2007/0285238 A1* | 12/2007 | Batra ............... G01K 1/024 340/572.1 |
| 2008/0030345 A1* | 2/2008 | Austin ............... A61B 19/44 340/572.8 |
| 2008/0059228 A1 | 3/2008 | Bossi |
| 2008/0097552 A1 | 4/2008 | Dicks et al. |
| 2008/0188813 A1 | 8/2008 | Miller et al. |
| 2008/0202978 A1 | 8/2008 | Saloman et al. |
| 2008/0203107 A1 | 8/2008 | Conley |
| 2008/0249468 A1 | 10/2008 | Edwards et al. |
| 2008/0312715 A1 | 12/2008 | Asirvatham |
| 2009/0030366 A1 | 1/2009 | Hochman |
| 2009/0040874 A1 | 2/2009 | Rooney |
| 2009/0108552 A1* | 4/2009 | Mann, III ............... B64F 1/364 280/79.3 |
| 2009/0120962 A1 | 5/2009 | Malorni et al. |
| 2009/0128330 A1* | 5/2009 | Monroe ............... A61M 5/002 340/568.1 |
| 2009/0149894 A1 | 6/2009 | Merry et al. |
| 2009/0164042 A1 | 6/2009 | Handfield |
| 2009/0184022 A1 | 7/2009 | Coe et al. |
| 2009/0187274 A1 | 7/2009 | Higham |
| 2009/0194104 A1 | 8/2009 | Van Sickle |
| 2009/0231132 A1 | 9/2009 | Shoenfeld |
| 2009/0294521 A1 | 12/2009 | de la Huerga |
| 2010/0010666 A1 | 1/2010 | Adams |
| 2010/0022953 A1 | 1/2010 | Bochenko et al. |
| 2010/0022987 A1 | 1/2010 | Bochenko et al. |
| 2010/0062748 A1 | 3/2010 | Steinmetz |
| 2010/0160857 A1 | 6/2010 | Pongpairochana et al. |
| 2010/0169111 A1 | 7/2010 | Brue et al. |
| 2010/0204659 A1 | 8/2010 | Bochenko et al. |
| 2010/0211005 A1 | 8/2010 | Edwards et al. |
| 2010/0252036 A1 | 10/2010 | Sutherland et al. |
| 2010/0300130 A1 | 12/2010 | Shoenfeld |
| 2010/0305750 A1 | 12/2010 | Conley |
| 2010/0318035 A1 | 12/2010 | Edwards et al. |
| 2011/0021140 A1 | 1/2011 | Binier |
| 2011/0148624 A1 | 6/2011 | Eaton |
| 2011/0166700 A1 | 7/2011 | Dunn |
| 2011/0231535 A1 | 9/2011 | Starnes |
| 2011/0234419 A1 | 9/2011 | Churbock et al. |
| 2011/0266929 A1 | 11/2011 | Michael |
| 2012/0003928 A1 | 1/2012 | Geboers |
| 2012/0052837 A1* | 3/2012 | Reich ............... H04W 4/001 455/404.2 |
| 2012/0130534 A1 | 5/2012 | Wurm |
| 2012/0182143 A1 | 7/2012 | Gaines |
| 2012/0253837 A1 | 10/2012 | Cashman |
| 2012/0259456 A1 | 10/2012 | Saltsov |
| 2012/0259458 A1 | 10/2012 | Barrett et al. |
| 2012/0274196 A1 | 11/2012 | Arceta et al. |
| 2012/0280815 A1 | 11/2012 | Edwards |
| 2012/0302990 A1* | 11/2012 | de Paula ............. A61M 5/1723 604/503 |
| 2012/0310410 A1 | 12/2012 | Adams |
| 2013/0030566 A1 | 1/2013 | Shavelsky et al. |
| 2013/0090594 A1 | 4/2013 | Palmer et al. |
| 2013/0131586 A1 | 5/2013 | Poutiatine et al. |
| 2013/0166066 A1 | 6/2013 | Dunn |
| 2013/0245545 A1 | 9/2013 | Arnold |
| 2013/0262184 A1 | 10/2013 | Jain et al. |
| 2014/0004808 A1* | 1/2014 | Li ............. H01Q 1/22 455/90.2 |
| 2014/0073262 A1 | 3/2014 | Gutierrez |
| 2014/0114277 A1 | 4/2014 | Eggert et al. |
| 2014/0142403 A1 | 5/2014 | Brumback et al. |
| 2014/0155827 A1 | 6/2014 | Ostrander et al. |
| 2014/0218537 A1 | 8/2014 | Nepo |
| 2014/0252927 A1 | 9/2014 | Denny |
| 2014/0357304 A1 | 12/2014 | Ostrander et al. |
| 2014/0379874 A1 | 12/2014 | Starr et al. |
| 2015/0078536 A1 | 3/2015 | Denny et al. |
| 2015/0105903 A1 | 4/2015 | Denny et al. |
| 2015/0251839 A1 | 9/2015 | Denny et al. |

FOREIGN PATENT DOCUMENTS

| | | |
|---|---|---|
| EP | 1 291 802 | 3/2003 |
| EP | 2926328 A1 | 10/2015 |
| HK | 1215749 | 9/2016 |
| IN | 1572/MUMNP/2015 A | 5/2016 |
| WO | WO 96/21925 | 7/1996 |
| WO | WO 03/043684 | 5/2003 |
| WO | WO 2005 004961 | 1/2005 |
| WO | WO 2007/081947 | 7/2007 |

OTHER PUBLICATIONS

International Search Report for PCT/US2013/072881 dated Feb. 26, 2014.
International Search Report for PCT/US2013/072878 dated Feb. 26, 2014.
International Search Report and Written Opinion dated Jan. 12, 2016 in PCT/US15/44911.
International Search Report and Written Opinion dated Feb. 1, 2016 in PCT/US15/49232.
Google Patents Search, Aug. 25, 2016, 2 pages.
International Preliminary Report on Patentability and Written Opinion from related PCT application PCT/US2015/044911 dated Feb. 14, 2017, 9 pages.
International Preliminary Report on Patentability in Related PCT Application PCT/US2015/049232 dated Mar. 23, 2017, 10 pages.

* cited by examiner

MEDICAMENT INFORMATION SYSTEM AND METHOD

CROSS REFERENCE TO RELATED APPLICATIONS

This application is a continuation of U.S. patent application Ser. No. 13/907,028, filed May 31, 2013, which claims the benefit of U.S. Provisional Application No. 61/732,753, filed on Dec. 3, 2012, the entire disclosure of which is incorporated herein by reference.

TECHNICAL FIELD

Various exemplary embodiments disclosed herein relate generally to administration of medicaments.

BACKGROUND

Some people suffer from medical conditions such as severe allergies that may result in anaphylaxis. Anaphylaxis may be treated by administration of epinephrine. Patients may be prescribed an auto-injector of epinephrine to treat sudden anaphylaxis.

Anaphylaxis, however, often leads to an emergency situation wherein epinephrine or other medication should be administered as soon as possible to prevent loss of life or other complications. Proper use of the auto-injector to treat anaphylaxis is therefore important. Patients with medical conditions that may result in anaphylaxis are often inexperienced at providing medical treatment. Use of an auto-injector may also be intimidating for some patients. Moreover, an emergency situation requiring treatment may arise at unexpected times or after a significant time from receiving the auto-injector and instructions for use from a doctor or pharmacist. Additionally, due to the unpredictable use of the auto-injector, the medicament may expire before the auto-injector is used. An expired medicament may not effectively treat anaphylaxis in an emergency situation.

SUMMARY

In light of the present need for various contingency planning in the administration of epinephrine and other medications, a brief summary of various exemplary embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

Various exemplary embodiments relate to a method of using an emergency medicament device. The method includes reading an ID tag from the medicament device using a mobile device; automatically requesting instructions for using the medicament device based on the ID tag; and displaying a video to a user of the mobile device, the video providing instructions for using the medicament device in accordance with approved labeling of the medicament device.

In various embodiments, the ID tag is a quick response (QR) code.

In various embodiments, the method further includes reading product information including an expiration date from the medicament device; transmitting the product information to an application server; and receiving a notification from the application server regarding the expiration date of the medicament device. The step of reading an expiration date may include photographing a printed expiration date on the medicament device; and recognizing characters in the printed expiration date. The product information may further include a lot number and the method may further include receiving a notification regarding a recall of the medicament device based on the lot number.

In various embodiments, the video is streamed from a remote application server.

In various embodiments, the method further includes receiving an indication that the medicament device has been used; and providing location information to emergency services.

In various embodiments, the method further includes sending registration information to an application server, the registration information including a request to track location information; receiving medicament device information for a registered medicament device including location information; and displaying a map including registered medicament device information.

Various exemplary embodiments relate to an electronic medicament device including: a reservoir configured to store an amount of medication for treating anaphylaxis; an administration component for administering the medication to a patient; a processor communicatively connected to a memory storing medicament device information; and an identification tag configured to be read by another device, the identification tag providing the medicament device information including identification of instructions for using the medicament device.

In various embodiments, the electronic medicament device includes a display device, wherein the processor is configured to display an alert via the display device when an expiration date associated with the amount of medication has been passed.

In various embodiments, the processor is configured to play audio instructions for administering the medication.

In various embodiments, processor is configured to control the amount of medication administered by the administration component.

In various embodiments, administration component is an auto-injector.

In various embodiments, the electronic medicament device further includes a communication interface, wherein the processor is configured to communicate with at least one remote system via the communication interface in response to the occurrence of an event, the event including at least one of; administration of the medication and expiration of the medication.

In various embodiments, the electronic medicament device further includes a temperature sensor configured to determine the current temperature of the medication, wherein the processor is configured to provide an indication that the current temperature is outside of an approved temperature range.

In various embodiments, the electronic medicament device further includes a short-range wireless communication interface, wherein the processor is configured to periodically attempt to connect to an external device via the short-range wireless communication interface and trigger an alarm responsive to the attempt to connect failing.

Various exemplary embodiments relate to an application server in communication with a mobile device, the application server including a processor and a memory, the application server configured to: receive a medicament device identifier scanned from an emergency medicament device containing epinephrine for the treatment of anaphylaxis using an application on the mobile device; and stream an instructional video to the mobile device, the instructional video providing instructions for using the medicament device in accordance with approved labeling of the medicament device.

In various embodiments, the application server is further configured to: receive registration information from the mobile device including an expiration date and lot number scanned from a medicament device and contact information; store the registration information in association with the contact information; determine an event associated with the registration information; and send a notification to the mobile device based on the event and the contact information.

In various embodiments, the event is one of an expiration of the medicament device and a recall of the medicament device.

In various embodiments, the application server is further configured to: periodically receive location information of the medicament device from the mobile device; update a database with the location information for the medicament device; receive a request for location information from a second device; determine whether the second device is allowed to access the location information for the medicament device based on the registration information; and provide medicament device information including the location information to the second device responsive to the second device being allowed to access the location information.

BRIEF DESCRIPTION OF THE DRAWINGS

In order to better understand various exemplary embodiments, reference is made to the accompanying drawings, wherein.

DETAILED DESCRIPTION

Figure 1:
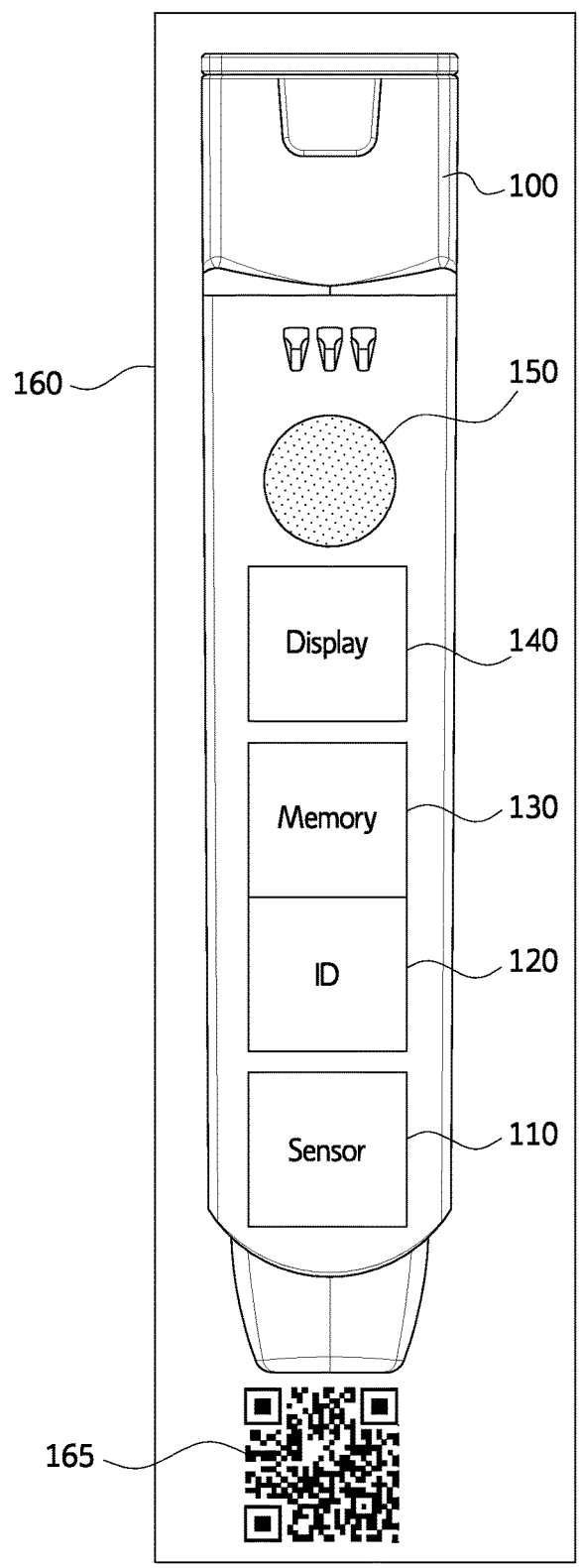
FIG. 1 illustrates an exemplary electronic medicament device.

Referring now to the drawings, in which like numerals refer to like components or steps, there are disclosed broad aspects of various exemplary embodiments.

FIG. 1 illustrates an exemplary electronic medicament device 100. The electronic medicament device 100 may include a medication for treating a condition, the medication being stored in a reservoir. In various exemplary embodiments, the electronic medicament device 100 includes an auto-injector for epinephrine or other administration component such as a non-auto-injector needle or controlled access panel for providing access to a solid medication stored in the reservoir. Medicaments 120 may include one or more medicaments for treating emergency or other medical conditions. In various exemplary embodiments, medicament device 120 may be auto-injectors for administering a dose of epinephrine. Suitable auto-injectors and associated devices and method are described by U.S. Pat. Nos. 4,031,893; 4,394,863; 4,484,910; 4,640,686; 4,678,461; 4,795,433; 4,832,682; 5,085,641; 5,092,843; 5,102,393; 5,354,286; 7,449,012; and 8,048,035, all of which are hereby incorporated by reference in their entireties for all purposes.

Medicament device 100 or packaging 160 may be imprinted with various medicament information. For example, medicament device 100 may include the name of the medicament, active ingredients, dosage, expiration date, lot ID, and product serialization number. The medicament information may be printed in a manner that is machine-readable. For example, the medicament information may be printed as a quick response (QR) code 170. The medicament information may also be printed as text that is easily recognized using optical character recognition (OCR). Packaging 160 may include a container such as a box or tube as well as any inserts or cards included within the packaging. It should be apparent that any information included on the medicament device 100 may instead be located on packaging 150. As will be discussed in further detail below, the medicament information may also be digitally encoded in a memory 130 of the medicament device.

The electronic medicament device 100 may further include sensor 110, ID tag 120, memory 130, display 140, and speaker 150. Although not illustrated, the electronic medicament device may include additional hardware such as, for example, a processor and/or additional communication interfaces. A processor may interconnect one or more of those components illustrated in FIG. 1. Such additional communication interface may include, for example, an interface for communication via wifi, a mobile carrier network, or satellite. Alternatively, the additional communication interface may include a wired communication interface.

Sensor 110 may detect activation of electronic medicament device 100. Sensor 110 may include a frangible element that completes or breaks an electronic circuit when electronic medicament device 100 is activated. Sensor 110 may provide a signal to ID tag 120 to perform an action in response to use of the medicament. Sensor 110 may alter memory 130 to indicate that the medicament device 100 is used and may log a time of use.

In various embodiments sensor 110 may include a temperature sensor. The temperature sensor may continuously measure the current temperature of the medication. The temperature sensor may provide the current temperature to a processor to compare to approved temperatures. In embodiments where the medication is epinephrine, the approved temperature range may be 15-30° C. An alarm may be generated by display 140 or speaker 150 if the current temperature is outside of the approved temperature range.

In various embodiments, sensor 110 may include a colorimetric sensor capable of determining the color of the medicament. For example, sensor 110 may be a spectrophotometer. The color of the medicament may be indicative of the quality of the medicament. For example, a medicament may turn from clear to pink or brown if the medicament becomes degraded.

ID tag 120 may include an RFID, NFC, or other tag for short range wireless communications. Such tags may be powered by passive energy and not require a battery. In various embodiments, ID tag 120 may include a battery powered wireless transmitter using, for example, Bluetooth. ID tag 120 may provide information from electronic medicament device 100 to a wireless reader such as, for example, wireless reader 140 or a NFC enabled mobile device. ID tag 120 may be connected to or include memory 130. In various embodiments, ID tag 120 may be located on packaging 160 rather than medicament device 100.

Memory 130 may store information regarding electronic medicament device 100. Memory 130 may include a nonvolatile memory such as a read-only memory (ROM) or an electronically erasable programmable read only memory (EEPROM). Information stored by memory 130 may include manufacture date, expiration date, medication, dose size, audio instructions, text instructions, other instructions, prescription information, re-order information, and emergency contact information.

Display 140 may include a display such as a LCD, LED array, or a single LED. Display 140 may display information about electronic medicament device 100. Display 140 may read and display any information stored in memory 130. For example, display 140 may display the expiration date of the medication. Display 140 may also display instructions for a user. In various embodiments, display 140 may illuminate, flash, or display a particular message in response to particular events such as the expiration of the medication, use of the medicament, or separation from another device such as case or a mobile device 220.

Speaker 150 may provide audio output. For example, speaker 150 may play pre-recorded instructions stored in memory 130. In various embodiments, ID tag 120 or another communication interface (not shown) may download or stream information from another device to be played by speaker 150. For example, the electronic medicament device 100 may stream information from an application server 250 or from a remote operator, either directly or via a mobile device 220

In various embodiments, the electronic medicament device 100 may be reusable. As such, the electronic medicament device 100 may receive a disposable cartridge or component set including the medication and/or a clean needle. Such cartridge or component set may include its own RFID tag or other means for communicating an expiration date or other information to the electronic medicament device 100 or mobile device 220.

In various embodiments, the processor or other component of the electronic medicament device 100 may alter the operation of the electronic medicament device 100 based on user information or other information. For example, the electronic medicament device 100 may provide different dosages based on a dosage prescribed to an authorized user. As another example, a user may input a patient weight, height, and/or body mass index (BMI) into a keypad of the electronic medicament device 100 or input information into a mobile device 220 and wirelessly transmit the user information to the medicament device 100. The processor may then calculate and administer an appropriate dosage based on the input factors. As another example, the processor may prevent or disable medicine administration when the user is not authorized for such administration.

Figure 2:
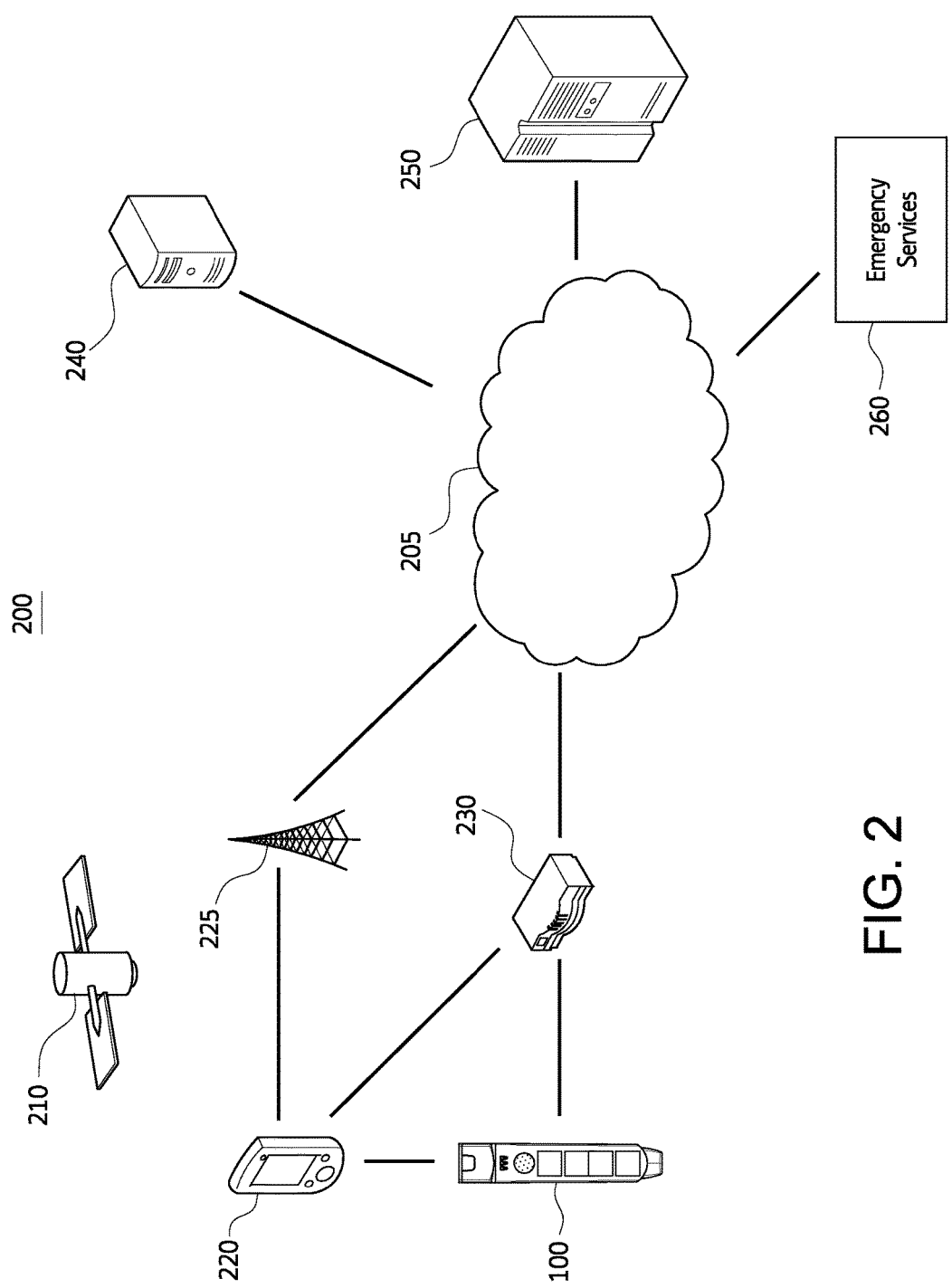
FIG. 2 illustrates an exemplary network environment for an electronic medicament device.

FIG. 2 illustrates an exemplary network environment 200 for electronic medicament device 100. Electronic medicament device 100 may interact with various elements of network environment 200 to provide emergency access and enhanced features. Network environment 200 may include a network 205, GPS satellites 210, mobile device 220, mobile base station 225, wireless router 230, medical server 240, central control 250, and emergency services 260.

Network 205 may be a digital network for communicating information. For example, network 205 may be the internet. Network 205 may transmit information between various end users and devices. Network 205 may also include telephone networks.

GPS satellites 210 may enable electronic medicament device 100, mobile device 220, and other devices to determine their respective physical locations. GPS satellites 210 may be geosynchronous satellites that broadcast signals. GPS enabled devices may use the signals from multiple satellites to determine their location. In various embodiments, GPS satellites 210 may include or be replaced by terrestrial location systems. For example, wi-fi access points may be used to detect the physical location of a device.

Mobile device 220 may be a device such as a smart phone, tablet computer, laptop, or any other computing device capable of executing applications and performing communication. In various embodiments, mobile device 220 is an NFC enabled mobile phone that can communicate using short range wireless protocols as well as local networking and mobile networks. In particular, mobile device 220 may communicate with a mobile network using mobile base station 225. Mobile device 220 may include location detecting services such as GPS.

Mobile device 220 may interact with the electronic medicament device 100 using RFID, NFC, or other wireless communication. Mobile device 220 may read medicament information that is either printed on medicament device 100 or stored in memory 130. For example, mobile device 220 may include a camera and application configured to read a QR code or printed text. Mobile device 220 may also read data from the memory 130 using a short-range wireless protocol such as RFID, NFC or Bluetooth. The short-range wireless communication may also be used by mobile device 220 to determine the presence of a medicament device 100. For example, mobile device 220 may periodically attempt to read the medicament device 100 and determine that the medicament device 100 is not present if the mobile device 220 is unable to read the medicament device 100.

Mobile device 220 may include an application specifically for interacting with electronic medicament device 100. Mobile device 220 may access memory 130 via ID tag 120 and read or write data. Mobile device 220 may detect changes in electronic medicament device 100 and perform actions in response. For example, mobile device 220 may detect that electronic medicament device 100 has been activated. Mobile device 220 may automatically contact emergency services 260 and allow a user to speak with emergency personnel, or mobile device 220 may provide a pre-recorded message to emergency services 260 indicating that the medicament has been activated to treat a condition of the patient. Mobile device 220 may also provide a location based on GPS information so that emergency personnel can locate the patient. The application may also interact with server 250 to provide additional medicament related information and services. For example, the application may provide disease information and news, medicament registration, reminders, product accessory information, medicament insert and patient information, and local allergy information.

ID tag 120 may be used to determine whether electronic medicament device 100 is within close proximity to a mobile device 220. ID tag 120 may periodically poll or be polled by a wireless reader in the mobile device 220. If the poll does not occur when expected, or the mobile device does not respond, electronic medicament device 100 may generate an alert. For example, electronic medicament device 100 may play a sound through the speaker 150 or flash the display 140 to alert a user. The alert may remind the user to keep the medicament close by in case of emergency. Mobile device 220 may also generate an alert if electronic medicament device 100 is not detected. Mobile device 220 may be configured to check for the presence of electronic medicament device 100 whenever the user enters or leaves a particular location. For example, mobile device 220 may generate an alert if a user leaves home without the electronic medicament device.

In various embodiments, the ID tag 120 may be used to actively search for electronic medicament device 100. Mobile device 220 may be configured to transmit a signal to ID tag 120 upon activation by a user. The signal may be received by ID tag 120 and cause the speaker 150 to produce an audible sound. The volume or pitch of the sound may vary depending on the strength of the received signal. Alternatively, mobile device 220 may detect a signal reflected by an ID tag 120 such as a passive RFID tag. Mobile device 220 may play an audible sound and vary the volume or pitch depending on the strength of the reflected signal.

Mobile device 220 may also contact emergency contacts. For example, mobile device 220 may email, message, or call any emergency contacts stored in memory 130 or within mobile device 220 when the electronic medicament device 100 is used or generates some other alert. Mobile device 220 may select contacts based on time of day or other available information.

Upon detection of an expired medicament or activation of the medicament, mobile device 220 may initiate ordering a replacement medicament Mobile device 220 may send an order to either control center 250 or medical server 240. The order may include patient and prescription information. Medical server 240 may determine whether the prescription includes refills, whether replacements are allowed without a prescription, or whether the patient has a valid or perpetual prescription for the medicament. Medical server 240 may automatically fulfill the order if the prescription is authorized. Alternatively, medical server 240 may schedule an appointment with the patient's doctor for a new prescription and to follow-up regarding the deployment of the medicament.

Wireless router 230 may be a wireless router providing connectivity to a local area network (LAN) and the internet. Wireless router 220 may be accessed electronic medicament device 100, and mobile device 220. Accordingly, wireless router 220 may provide these devices with internet access to send and receive data.

Medical server 240 may be a server operated by a health care provider, health insurance provider, or government health agency. Medical server 240 may store patient information. Medical server 240 may provide patient information to authorized devices such as the patient's mobile device 220, control center 250, and emergency services 260. Medical server 240 may be configured to receive and process particular messages from electronic medicament device 100, mobile device 220, and control center 250. For example, medical server 240 may be configured to verify prescriptions and order refills.

Application server 250 may be a computer server operated by a medicament manufacturer or other third party. The application server 250 may provide a downloadable application for execution on a mobile device. The application server 250 may also provide support for the downloadable application and/or a web application. The application server 250 may include a database of registered medicament information provided by patients who opt to register the medicament device 100. The application server 250 may provide various services accessible via the application. The application server 250 may provide audio and/or video instructions that may be downloaded or streamed to a mobile device. The application server 250 may provide information to a mobile device based on a registered medicament device. For example, the application server 250 may track expiration dates and provide notification of approaching expiration dates. In various embodiments, the application server 250 may provide a tracking system enabling a registered user to track the last known physical location of registered medicament devices.

The electronic medicament device 100 may provide usage information to the application server 250 which, in turn, may process the data for various uses. For example, the application server 250 may provide the processed usage data to an application executing on a mobile device, such as mobile device 220. Such application may provide, for example a map indicating where the user has administered the electronic medicament device 100 and/or other electronic medicament devices 100. Such application could also present a real-time alert as to when the electronic medicament device 100 has been used, including location information. The application may also provide historical data and analysis of electronic medicament device 100 usage events such as event listings and graphs. As another example, the application server 250 may track disposal and/or recycling of medicament device 100. A disposal or recycling facility may scan medicament information including a lot ID and product serialization number from medicament device 100. The disposal or recycling facility may send the scanned medicament information to application server 250 and/or medical server 240 for reconciliation with registered medicament device 100.

Figure 3:
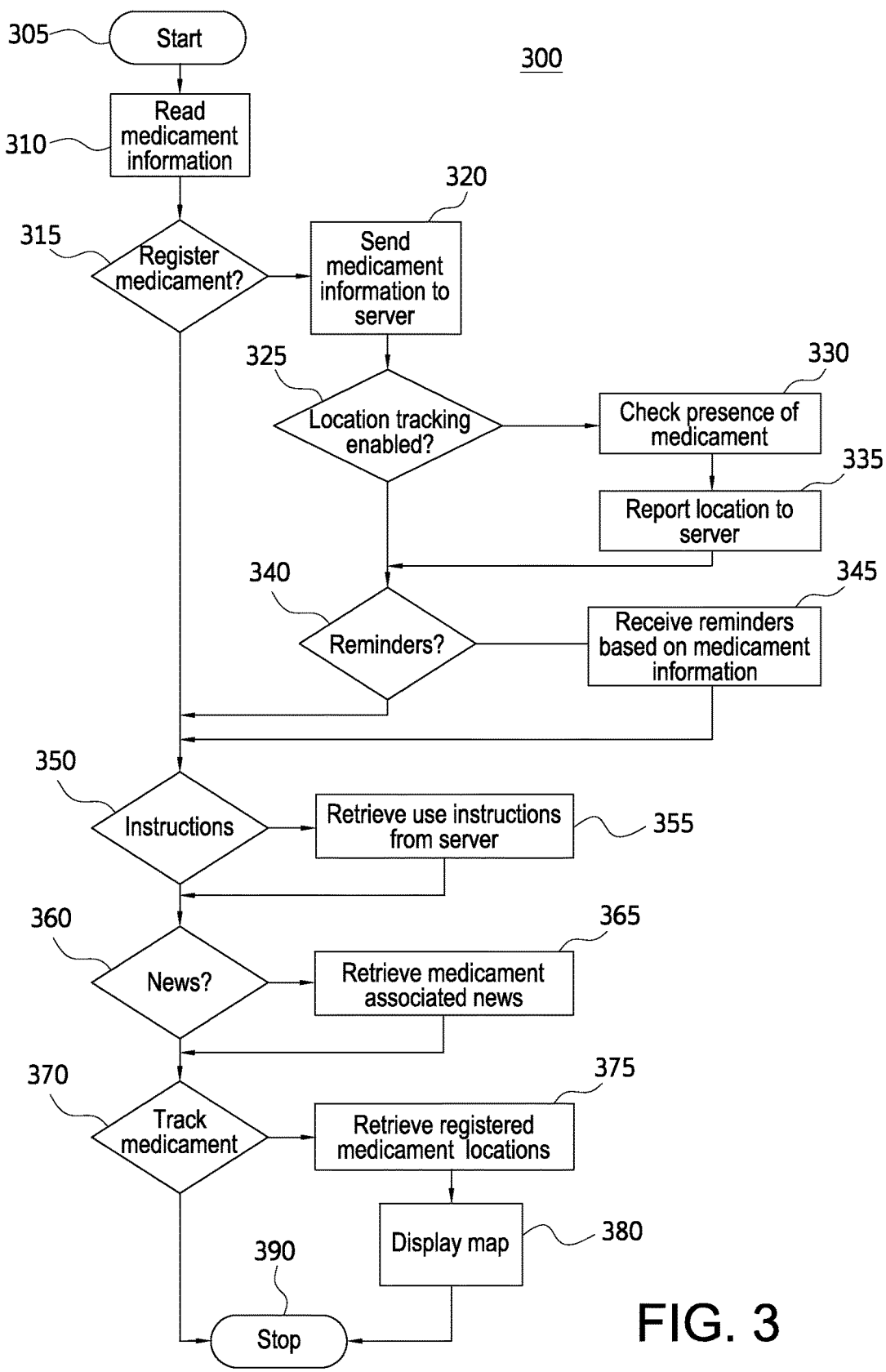
FIG. 3 illustrates a flowchart showing an exemplary method performed by a mobile device.

FIG. 3 illustrates a flowchart showing an exemplary method 300 performed by a mobile device 220. Mobile device 220 may include an application configured to cause the processor and other components of mobile device 220 to perform the steps of the method 300. The method 300 may begin at step 305 and proceed to step 310.

In step 310, the mobile device 220 may read medicament information from the medicament device 100. In various embodiments, the mobile device 220 may use a camera take a picture of medicament device 100 or the packaging thereof. For example, a user may take a photograph of the expiration date, lot number, and serialization number, or take a photograph of a QR code. The mobile device 220 may analyze the photograph to determine medicament information. The mobile device 220 may also forward the photograph to an application server 250 for analysis. In various embodiments, the mobile device 220 may read the medicament information from the memory 130.

In step 315, the mobile device 220 may determine whether a user wishes to register the medicament device 100. The mobile device 220 may present a user interface providing an explanation of the benefits of registration an option to register. The user interface may also provide the ability for the user to enter contact information or to manually enter medicament information. If the user chooses to register the medicament device 100, the method 300 may proceed to step 320. If the user chooses not to register the medicament device 100, the method 300 may proceed to step 350.

In step 320, the mobile device 220 may send medicament information to the server. The mobile device 220 may send medicament information read from the medicament device 100, packaging, and/or memory 130. The mobile device 220 may also send user information entered by the user. In various embodiments, the user may update an existing registration with a new medicament device 100. Accordingly, the server 150 may already have user information and only a user identifier may be sent with the medicament information. In various embodiments, the mobile device 220 may send the medicament information to medical server 240 in addition to application server 250. For example, a government health agency may collect medicament information. Application server 250 may also forward the medicament information to medical server 240.

In step 325, the mobile device 220 may determine whether the user wishes to register for a location tracking service. As will be described in further detail below, the location tracking service may monitor the location of the medicament device 100 and help a user find the device 100 if it is lost or activated. The mobile device 220 may prompt a user to enter additional information useful for tracking the location of the medicament device 100 such as a phone number of an additional mobile device 220 that may be used to track the medicament device 100. The additional mobile device 220 may be, for example, a mobile device usually carried by a child who has been prescribed the medicament device 100. If the user enables location tracking, the method 300 may proceed to step 330. If the user opts out of location tracking, the method 300 may proceed to step 340.

In step 330, the mobile device 220 may check for the presence of the medicament device. In various embodiments, the mobile device 220 may use a short-range wireless communication protocol such as Bluetooth to poll the medicament device. If the medicament device 100 is present, the mobile device 220 may establish a connection with the medicament device 100 and receive additional information.

In step 335, the mobile device 220 may report the location of the medicament device 100 to the server 150. If the mobile device 220 detected the presence of the medicament device 100 in step 330, the mobile device may report the location of the mobile device 220 as the location of the medicament device 100. If the medicament device 100 is not detected, the mobile device 220 may report a missing medicament device having no known location or report the last known location of the medicament device 100.

In step 340, the mobile device 220 may determine whether a user wishes to receive reminders regarding the medicament device 220. The mobile device 220 may present a user interface displaying information regarding available reminders. The user of the mobile device may select those reminders he or she would like to receive. Exemplary reminders regarding a medicament device may include a reminder to replace an expired medicament device, a reminder to review instructions, a reminder to obtain a new prescription, a reminder to perform a medical test, and a reminder to take a periodic dose from the medicament device. The mobile device 220 may send the selected reminders to server 150, which may monitor for events related to the reminders. In step 345, the mobile device 220 may receive a reminder from the server 150 based on medicament information. In various embodiments, the reminder may be received via simple messaging service (SMS), email, or an application based messaging system.

In step 350, the mobile device 220 may determine whether the user wishes to receive instructions. The user may indicate a desire to receive instructions by selecting a button within the application. In various embodiments, the mobile device 220 may automatically request instructions based on the user scanning a QR code or taking a picture of the medicament device. If the user desires to receive instructions, the method 300 may proceed to step 355. If the user does not desire to receive instructions, the method 300 may proceed to step 360. In step 355, the mobile device 220 may request the instructions from the server 250. The request may include information identifying the medicament device 100. In various embodiments, the request may include only a name or identifier of the medicament device 100 and not particular information such as a lot number, product serialization number, or expiration date. In step 355, the mobile device 220 may receive instructions from server 250. The instructions may be in the form of a video streamed from the application server 240. The instructions may also include audio or written instructions.

In step 360, the mobile device 220 may determine whether the user wishes to receive news regarding the medicament device 100. The user may indicate a desire to receive news by selecting a button within the application. If the user desires to receive news, the method 300 may proceed to step 365. If the user does not desire to receive news, the method 300 may proceed to step 370. In step 365, the mobile device 220 may receive news updates from the server 250. The news updates may be pushed to the mobile device 220 based on the identified medicament device.

In step 370, the mobile device 220 may determine whether the user desires to track a medicament device 100. The tracking service may require registration of the medicament device with server 250. The user may indicate a desire to track a medicament device by selecting a button within the application. In various embodiments, tracking a medicament device 100 may be initiated by an application server 250 in response to an event concerning the device. For example, use of a registered medicament device 100 may be reported to the application server 250 by a patient's mobile device. The application server 250 may then push a notification to another user device 220, such as a device of a parent or other emergency contact, and provide tracking information. If the user desires to track a medicament device 100, the method 300 may proceed to step 375. If the user does not desire to track a medicament device, the method 300 may proceed to step 390, where the method 300 ends.

In step 375, the mobile device 220 may retrieve information regarding registered medicament devices 100 including location information. The mobile device 220 may require the user to enter a password or perform other security operations to ensure only the registered user has access to the medicament device information. The mobile device 220 may present a list of medicament devices 100 registered to the user or may request information regarding all registered medicament devices. The application server 250 may receive the request and extract medicament device information from a database. The application server 250 may also attempt to update the medicament device locations by polling other mobile devices associated with registered medicament devices for current medicament device information.

The mobile device 220 may receive the medicament information from the server 250. The medicament information may include a location, which may be, for example, longitude and latitude coordinates or a street address. The medicament information may also include information such as the current temperature of the medicament device, the time of the last use of the medicament device, and a number of doses remaining in the medicament device. In step 380, the mobile device 220 may present the medicament device information to the user as a map. The map may indicate the current location of the medicament device 100 as well as the current location of the mobile device 220.

Figure 4:
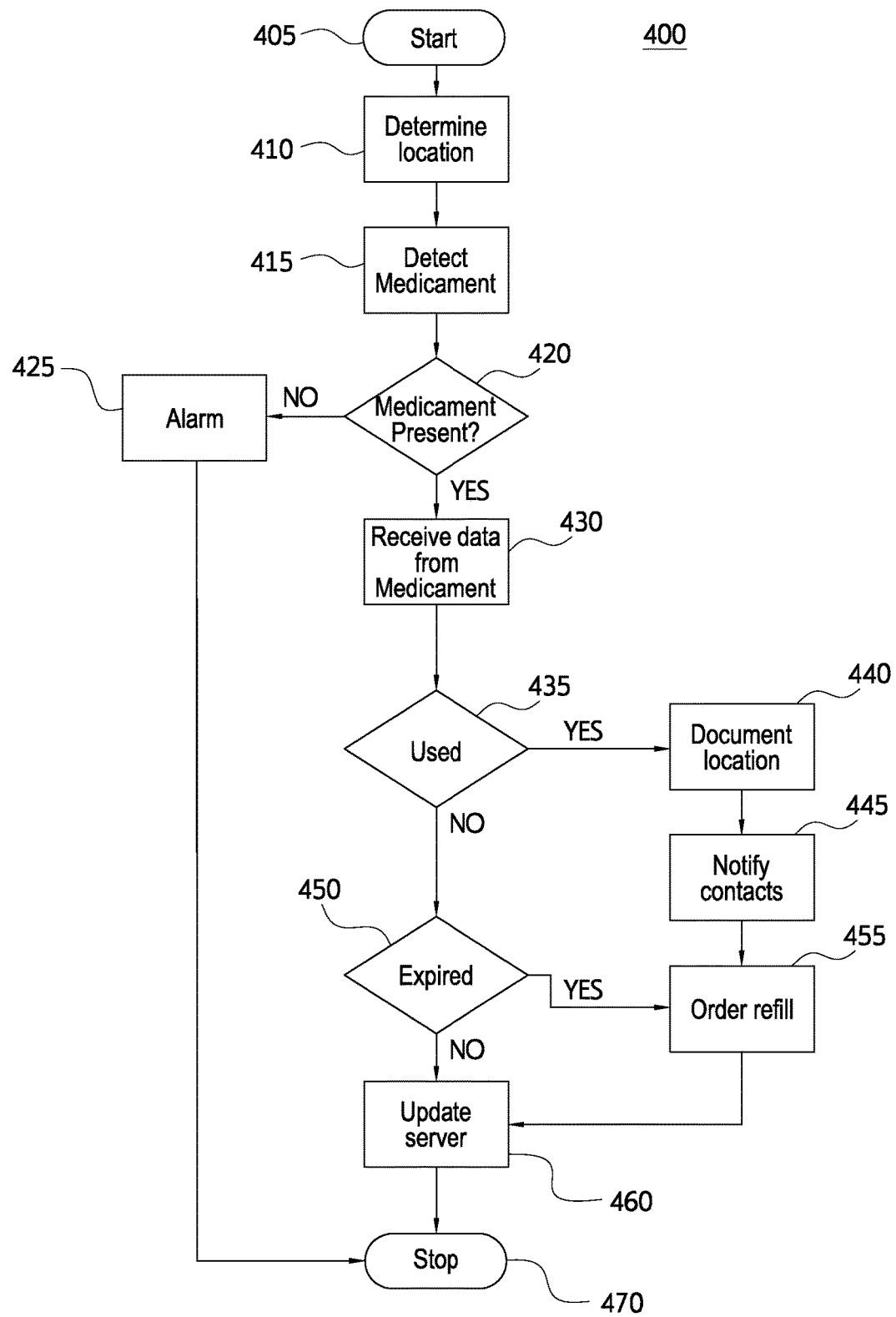
FIG. 4 illustrates a flowchart showing an exemplary method of monitoring a medicament.

FIG. 4 illustrates a flowchart showing an exemplary method 400 of monitoring a medicament. The method 400 may be performed by a mobile device 220 in communication with an electronic medicament device 100. The method 400 may be performed as step 330 of method 300 illustrated in FIG. 3.

The method 400 may begin at step 405 and proceed to step 410. In step 410, the mobile device 220 may determine its location. In various embodiments, mobile device 220 may use the location to determine whether to proceed with the method. For example, the mobile device 220 may discontinue the method if the mobile device is in a designated location, or the mobile device may delay the method until a change in location is detected.

In step 415, the mobile device 220 may detect any electronic medicament devices nearby. Mobile device 220 may use RFID, NFC, Bluetooth or another close range protocol to poll nearby tags 120 on a medicament device. Mobile device 220 may be configured to poll one or more specific electronic medicament devices with identifiers known by mobile device 220. In step 420, mobile device 220 may determine whether an electronic medicament device 100 is present. If no medicament device is present, the method may proceed to step 425. If a medicament device is detected, the method may proceed to step 430.

In step 425, the mobile device 220 may generate an alarm. The alarm may indicate any particular medicament device that was not detected. The alarm may include a message identifying the medicament device by name or by a condition that it treats. If the mobile device performs method 400 frequently, it may be likely that the medicament device is nearby, although out of range of the short range wireless protocol. Accordingly, a user may be reminded to retrieve the medicament device. The mobile device 220 may also generate a message to another mobile device. For example, the mobile device 220 may send an SMS message or email to a parent, guardian, or other emergency contact indicating that the medicament device 100 has been separated from the mobile device 220. The method 400 may then proceed to step 460, where the method ends.

In step 430, the mobile device 220 may receive data from the medicament device. Mobile device 220 may send a read command to read data from memory 130. In various embodiments, mobile device 220 may receive data from the electronic medicament device 100 when sensor 110 determines that the device 100 has been activated. In step 435, mobile device 220 may determine whether the medicament device 100 has been used. Mobile device 220 may determine the status of sensor 110 or parse data received in step 430. If the medicament device has been used, the method may proceed to step 440. If the medicament device has not been used, the method may proceed to step 450.

In step 440, mobile device 220 may document the current location of the mobile device. The location of the mobile device may be used to identify the location of device usage. In step 445, the mobile device may notify emergency contacts. Mobile device 220 may contact emergency services, for example, by dialing 911. The mobile device 220 may turn on a speaker phone to allow a user, who may be suffering from anaphylaxis or another medical condition to speak to an emergency dispatcher. If mobile device 220 does not receive any voice input, mobile device 220 may play a recorded message indicating that the electronic medicament device has been activated at the stored location. Mobile device 220 may also contact other people. For example, mobile device 220 may call, email, or message emergency contacts stored in mobile device 220 or memory 130.

In step 450, mobile device 220 may determine whether the electronic medicament device 100 is expired. Mobile device 220 may compare an expiration date received from the electronic medicament device 100 to the current date. In various embodiments, the mobile device 220 may also have the ability to read the quality of the medicament. For example, mobile device 220 may read information from a sensor 110 in medicament device 100. The sensor 110 may determine that the medicament has expired early if, for example, the medicament device 100 was stored at an inappropriate temperature or has changed properties such as colors. In various embodiments, the mobile device 220 may be able to determine the quality of the product. For example, the camera of the mobile device may act as a spectrophotometer to measure the color of the medicament. Alternatively, the mobile device 220 may transmit a picture of the medicament device to application server 250 for spectrophotometric analysis. The medicament device 100 may include a transparent window and colored markings to assist with the spectrophotometric analysis. The mobile device 220 may determine that the medicament has expired early if the medicament exhibits a certain property. If the medicament device is expired, the method may proceed to step 455. If the medicament device is not expired, the method may proceed to step 450.

In step 455, the mobile device 455 may initiate an order for a refill or replacement electronic medicament device. Mobile device 220 may send an order to control center 250 and/or medical server 240. The method may then proceed to step 460.

In step 460, the mobile device 220 may update an application server 250 with information regarding the medicament device 220. The application server 250 may use the updated information to provide up to date information to other users associated with a registered medicament device. For example, the updated information may be used to provide the tracking service described above. The updated information may also be used by the application server 250 to generate notifications regarding local conditions such as allergy and asthma alerts. The application server 250 may provide such alerts as news to users who have registered medicament devices for treating the same condition. The method may proceed to step 470, where the method may end.

According to the foregoing, various exemplary embodiments provide for systems and methods for distributing medicaments. In particular, by providing remote access to a medicament storage case, medicaments can be provided to patients in an emergency.

It should be apparent from the foregoing description that various exemplary embodiments of the invention may be implemented in hardware and/or firmware. Furthermore, various exemplary embodiments may be implemented as instructions stored on a machine-readable storage medium, which may be read and executed by at least one processor to perform the operations described in detail herein. A machine-readable storage medium may include any mechanism for storing information in a form readable by a machine, such as a personal or laptop computer, a server, or other computing device. Thus, a machine-readable storage medium may include read-only memory (ROM), random-access memory (RAM), magnetic disk storage media, optical storage media, flash-memory devices, and similar storage media.

It should be appreciated by those skilled in the art that any block diagrams herein represent conceptual views of illustrative circuitry embodying the principals of the invention. Similarly, it will be appreciated that any flow charts, flow diagrams, state transition diagrams, pseudo code, and the like represent various processes which may be substantially represented in machine readable media and so executed by a computer or processor, whether or not such computer or processor is explicitly shown.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A system for receiving a medicament administration component and for communicating with a mobile device information associated with the medicament administration component, the system comprising:
   a medicament device configured to receive an epinephrine auto-injector;
   a communication interface coupled with the medicament device configured to wirelessly communicate with a mobile device information associated with a location of the medicament device;
   a temperature sensor coupled with the medicament device configured to detect a temperature associated with the medicament device;
   an indicator coupled with the medicament device configured to illuminate to provide a visual alert to a user;
   a sound source coupled with the medicament device configured to play a sound to provide an audible alert to the user; and
   a non-transitory computer readable medium comprising instructions stored thereon that when executed by at least one processor of the mobile device perform a process comprising:
      identifying emergency contacts and a notification message that are stored, prior to the medicament device being used, in a memory of the mobile device,
      receiving a communication from the remotely located medicament device, and
      in response to determining, from the communication and independently of input received by the mobile device from a user of the mobile device to initiate a call, that the medicament device is being used or has been used, causing the mobile device to initiate communication with the identified emergency contacts via a telecommunication network and to transmit the identified notification message.

2. The system of claim 1, wherein the communication interface is configured to transmit information associated with the medicament device to the mobile device that allows for determining proximity of the medicament device to the mobile device.

3. The system of claim 1, wherein the communication interface is configured to receive information from the mobile device that allows for determining proximity of the medicament device to the mobile device.

4. The system of claim 1, further comprising a sensor coupled with the medicament device configured to detect use of the medicament device, wherein information associated with the use of the medicament device is wirelessly communicated via the communication interface to the mobile device in response to detecting use of the medicament device.

5. The system of claim 1, wherein the communication interface is configured to transmit to the mobile device information associated with the detected temperature of the medicament device.

6. The system of claim 1, wherein the communication interface comprises an electronic tag.

7. The system of claim 1, wherein the communication interface comprises a memory configured to be read by the mobile device.

8. The system of claim 1, wherein the communication interface comprises a Bluetooth wireless transmitter.

9. The system of claim 1 in combination with a packaging into which the apparatus is placed.

10. The system of claim 9 wherein the packaging comprises a tube.

11. A non-transitory computer readable medium comprising instructions stored thereon that when executed by at least one processor of a mobile device perform a process for monitoring a medicament administration component, the process comprising:
    wirelessly communicating with a medicament device that contains an epinephrine auto-injector and that is located remotely from the mobile device;
    based at least on the wireless communication, determining whether the medicament device is within close proximity of the mobile device;
    generating an alert with the mobile device in response to determining that the medicament device is not within close proximity of the mobile device;
    based at least on the wireless communication and independently of input received by the mobile device from a user of the mobile device to initiate a call, determining whether the medicament device is being used or has been used;
    identifying emergency contacts and a notification message that are stored, prior to the medicament device being used, in a memory of the mobile device;
    in response to determining that the medicament device is being used or has been used, causing the mobile device to initiate communication with the identified emergency contacts via a telecommunication network and to transmit the identified notification message; and
    displaying a video on the mobile device that includes instructions on how to use the epinephrine auto-injector.

12. The non-transitory computer readable medium of claim 11, wherein the process further comprises determining whether a detected temperature of the medicament device is outside a temperature range.

13. The non-transitory computer readable medium of claim 11, wherein the process further comprises, based at least on the wireless communication, displaying information regarding a current temperature of the medicament device.

14. The non-transitory computer readable medium of claim 11, wherein generating an alert with the mobile device comprises displaying a message with the mobile device.

15. The non-transitory computer readable medium of claim 11, wherein wirelessly communicating with a medicament device comprises reading a memory of the medicament device.

16. The non-transitory computer readable medium of claim 11, wherein the process further comprises registering the medicament device for a location tracking service.

17. The non-transitory computer readable medium of claim 11, wherein the process further comprises location tracking the medicament device and displaying the location of the medicament device on the mobile device.

18. The non-transitory computer readable medium of claim 11, wherein the process further comprises:
    determining whether the epinephrine auto-injector is expired; and generating an alert with the mobile device in response to determining that the epinephrine auto-injector is expired.

19. The non-transitory computer readable medium of claim 11, wherein the process further comprises notifying emergency contacts through the mobile device in response to determining that the medicament device has been separated from the mobile device.

20. The non-transitory computer readable medium of claim 11, wherein the process further comprises playing an audible message on the mobile device in response to determining that the medicament device is being used or has been used.

* * * * *